United States Patent [19]
de Vries et al.

[11] Patent Number: 5,097,129
[45] Date of Patent: Mar. 17, 1992

[54] SURFACE CONTAMINATION DETECTION USING INFRARED-TRANSPARENT FIBERS OR ATTENUATED TOTAL REFLECTION CRYSTALS

[75] Inventors: Mattanjah S. de Vries, Los Gatos; William G. Golden, Morgan Hill; Heinrich E. Hunziker, Saratoga, all of Calif.

[73] Assignee: International Business Machines Corporation, Armonk, N.Y.

[21] Appl. No.: 623,636

[22] Filed: Dec. 6, 1990

[51] Int. Cl.$^5$ .............................. G01N 21/90
[52] U.S. Cl. .................... 250/338.1; 250/227.14; 250/227.18; 250/227.19; 250/339; 250/341; 360/97.03
[58] Field of Search .................. 250/227.18, 227.19, 250/227.14, 341, 339, 338.1; 356/300, 133; 360/97.02, 97.03, 97.04

[56] References Cited

U.S. PATENT DOCUMENTS

| | | | |
|---|---|---|---|
| 3,515,490 | 6/1970 | Dreyfus et al. | 356/244 |
| 4,303,859 | 12/1981 | McCue | 250/338.1 |
| 4,642,715 | 2/1987 | Ende | 360/97.02 |
| 4,835,389 | 5/1989 | Doyle | 250/343 |

FOREIGN PATENT DOCUMENTS

| | | | |
|---|---|---|---|
| 58-151542 | 9/1983 | Japan | 356/51 |
| 62-71083 | 4/1987 | Japan | 360/97.04 |

OTHER PUBLICATIONS

T. Mookherji and P. N. Peters, "*Application to contaminants:* Internal reflection spectroscopy," *Research/Development* (Oct. 1973) pp. 20-22 and 24.

Shimon Simhony, Abraham Katzir and Edward M. Kosower, "Fourier Transform Unfrared Spectra of Organic Compounds in Solution and as Thin Layers Obtained by Using an Attenuated Total Interanl Reflectance Fiberoptic Cell", Published in *Anal. Chem., vol. 60 (1988), pp. 1908-1910.*

*Primary Examiner*—Constantine Hannaher
*Attorney, Agent, or Firm*—Thomas R. Berthold; John D. Crane; Henry E. Otto

[57] ABSTRACT

Airborne contaminants within a substantially sealed enclosure are detected and measured, in situ, without interrupting the operation of moving parts within the enclosure. At least one infrared (IR)-transparent attenuated total reflection (ATR) element, such as an optical fiber, optical fiber bundle, or ATR crystal, is disposed in the enclosure to collect or react with contaminants. An IR source is optically coupled to one part of the element, and an IR detector is optically coupled to another part of the element. The source and detector, in combination, respond to changes in intensity at the wavelengths of the IR radiation transmitted by the element to identify the contaminants and quantities thereof that settle on the element or compounds that have formed thereon. The source may be a continuous source (such as a black body) and the detector an IR spectrometer. Or, the source may be a diode laser and the detector an IR radiation detector. The sealed enclosure may be the housing of a head-disk assembly of a disk file.

Alternatively, the apparatus may include an IR-transparent ATR element disposed within the housing and an IR spectrometer optically coupled to a radiation output surface of the element for sensing emission emerging from the element. One end of the element may be reflection coated to increase the radiation output.

38 Claims, 2 Drawing Sheets

# SURFACE CONTAMINATION DETECTION USING INFRARED-TRANSPARENT FIBERS OR ATTENUATED TOTAL REFLECTION CRYSTALS

This invention relates to an apparatus and method for detecting and measuring airborne surface contaminants, and more particularly to an apparatus and method using infrared-transparent attenuated total reflection elements (such as optical fibers or attenuated total reflection crystals) for chemically analyzing, in situ, contaminants that settle on the element inside a substantially sealed enclosure, such as the housing of a head-disk assembly of a magnetic recording disk file.

BACKGROUND OF THE INVENTION

Chemical contamination is a critical concern for magnetic recording. As the dimensions of the head-disk interface decrease, ever smaller amounts of contamination can cause it to fail. It is desirable to monitor the internal condition of disk packs in order to facilitate preventive maintenance. In so doing, disk drive failures can be anticipated or avoided by identifying an unacceptable level of contamination. Currently, it is very difficult to monitor the deposition of aerosols and low vapor pressure "environmental" chemicals, such as complex organics emanating from greases, oils, air conditioning systems, gaskets, plastic enclosures, etc. It is presently necessary to open and disassemble a head-disk assembly (HDA) in order to analyze contaminants which settle on the internal surfaces.

Attenuated total reflection (ATR) is a well-known principle in infrared (IR) spectroscopy. A paper entitled "Fourier Transform Infrared Spectra of Organic Compounds in Solution and as Thin Layers Obtained by using an Attenuated Total Internal Reflectance Fiber-Optic Cell", published in Anal. Chem. 1988 at pp. 1908-1910 discloses the use of infrared-transparent optical fibers as an ATR device for measuring the composition of liquids and solids.

No prior art known to applicants, however, teaches an apparatus or method for detecting and measuring airborne surface contaminants by using the ability of thin IR-transparent optical fibers or ATR crystals to trap airborne contaminants in combination with using IR spectroscopy or attenuated total reflection techniques to identify and measure surface deposits as minute as a fraction of a monolayer.

There is a need for a means and method to measure airborne contaminants in situ within a sealed environment especially one containing moving parts, such as a disk file, without interrupting its operation in any way.

SUMMARY OF THE INVENTION

Airborne contaminants within a substantially sealed enclosure are detected and measured, in situ, without interrupting the operation of moving parts within the enclosure. At least one infrared (IR)-transparent attenuated total reflection (ATR) element, such as an optical fiber or ATR crystal, is disposed in the enclosure to collect contaminants. An IR source is optically coupled to one part of the element, and an IR detector is optically coupled to another part of the element. The source and detector, in combination, respond to changes in intensity at the wavelengths of the IR radiation transmitted by the element to identify the contaminants and quantities thereof that settle on the element. The source may be a continuous source (such as a black body) and the detector an IR spectrometer. Or, the source may be a diode laser and the detector an IR radiation detector. The sealed enclosure may be the housing of a head-disk assembly of a disk file.

Alternatively, the apparatus may include an IR-transparent ATR element disposed within the housing and an IR spectrometer optically coupled to a radiation output surface of the element for sensing emission emerging from the element. One end of the element may be reflection coated to increase the radiation output.

DESCRIPTION OF PREFERRED EMBODIMENTS

Figure 1:
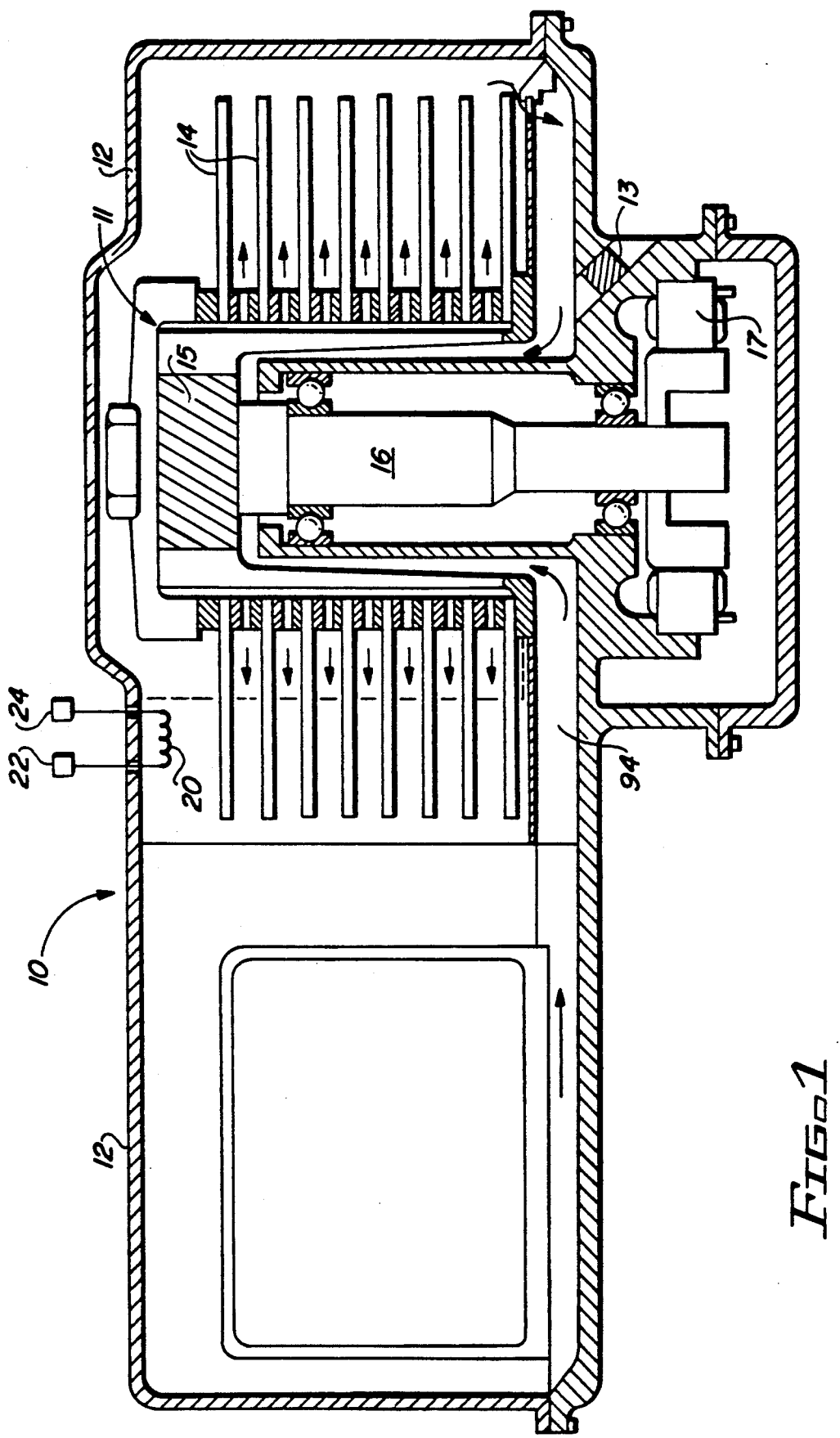
FIG. 1 is a vertical sectional view of a magnetic recording disk file embodying one implementation of the invention utilizing IR-transparent fibers.

As illustrated in FIG. 1, a magnetic recording disk file 10 embodying the invention comprises a head-disk assembly (HDA) 11. HDA 11 is contained within a housing 12 that is sealed except for an optional breather port 13. HDA 11 comprises a plurality of disks 14 mounted as a stack on a hub 15 that is rotated by a shaft 16 driven by a motor 17. An actuator (not shown) is movable radially in conventional manner for writing and reading magnetic indicia on a selectable one of the tracks on a selectable disk 14. This disk file, as thus far described, may be substantially identical with that described in U.S. Pat. No. 4,780,766, if more detailed description is desired.

According to one embodiment of the invention, at least one initially clean infrared (IR)-transparent optical fiber 20 (best shown in FIG. 2) is disposed, preferably coiled, within housing 12 such that a considerable length of the fiber(s) is exposed to that airspace within the housing where the probability of trapping contaminants is highest. The revolving disks 14 create internal air circulation within the housing. Thus, the actual location where the probability of trapping contaminants is highest depends on air movement and details of the enclosure. As illustrated, one end of each fiber 20 extends in sealed relation through an opening or port 21 in a wall of the housing 12 and is optically coupled to a continuous source 22 of IR radiation, such as a black body. The other end of each fiber 20 extends in sealed relation through a port 23 and is optically coupled to an IR spectrometer 24 (preferably a Fourier Transform IR (FTIR) spectrometer).

In operation, the spectrum of the initially clean fiber 20 (i.e., the "reference" spectrum) is stored as a series of contiguous points by the FTIR spectrometer 24 in conventional manner. Thereafter, whenever a contamination check is to be conducted, the then spectrum of the IR radiation exiting through port 23 is measured, and the reference spectrum is subtracted therefrom to provide a "residual" spectrum. The frequencies of absorption peaks in this residual spectrum identify the contaminant(s) that have settled on each fiber 20, and the intensity of absorption indicates the amount of contaminant(s).

The IR-transparent fibers 20 have the ability, as heretofore noted, to trap airborne contaminants, such as aerosols or vapors. This ability can be enhanced by coating the fiber with a film that traps aerosols and vapors by sticking, absorption or chemical reaction. Many internal reflections are generated within the unclad fibers. Thus, using ATR techniques, spectrometer 24 identifies, from the spectrum of IR radiation exiting through port 23, the nature and quantities of the airborne contaminants that settle on the portion of the fiber(s) within the housing as the spectra of detected IR radiation changes as the fiber becomes contaminated.

Figure 2:
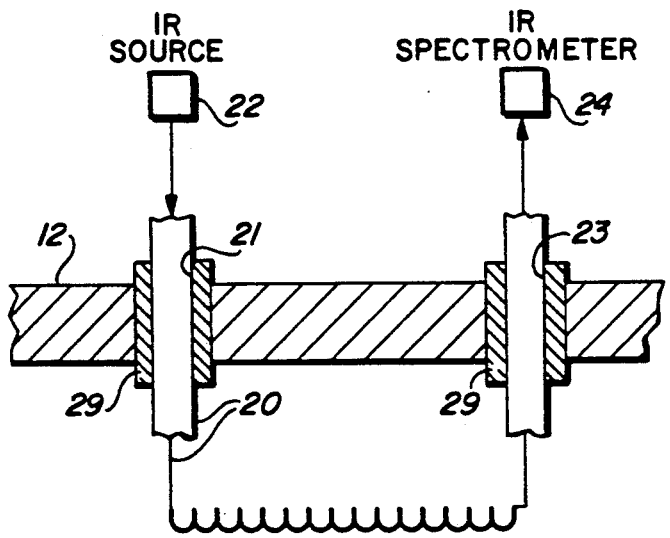
FIG. 2 is a fragmentary view, to enlarged scale, of a portion of the disk file shown in FIG. 1.

As a variation of the embodiment of FIG. 2, one end of optical fiber 20 is provided with a reflectance coating; the IR source 22 is eliminated; and the noncoated end of fiber 20 is optically coupled to IR spectrometer 24 to detect the IR emission originating from the surface of the fiber.

Figure 3:
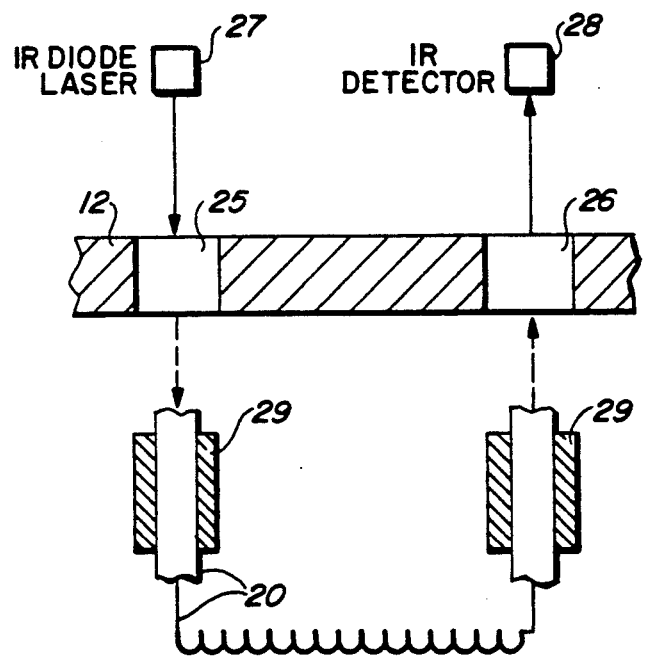
FIG. 3 is a fragmentary view, to enlarged scale, showing a variation of the implementation depicted in FIGS. 1 and 2.

If preferred, instead of passing the fiber ends through housing 12 and physically as well as optically coupling the fiber ends to the source 22 and spectrometer 24, the ends of each fiber 20 can be optically (but not physically) coupled, as illustrated in FIG. 3. In such case, the fiber ends would terminate within the housing behind transparent windows 25,26 located in openings in a wall of the housing. As illustrated in this embodiment of FIG. 3, the light source 22 is a tunable IR diode laser 27, and the IR radiation is sensed using an IR detector 28. Tunable diode laser 27 is initially tuned to one (reference) frequency at which no absorption occurs for the particular contaminant to be tested for. Thereafter, the ratio of the measured absorption intensity at the selected frequency to that at the reference frequency indicates the amount of that particular contaminant.

In any event, whether physically and optically or just optically coupled, measurement of deposits can be optimized by employing a bundle of optical fibers 20. This increases the surface area on which contaminants can settle and which can be sampled by the IR radiation. The average number of reflections per unit length of each fiber can be maximized by controlling the thickness and length of the fiber.

Chalcogenide glass fibers with a useful spectral range from 2-11 microns transmit a large part of the IR wavelength region that is of spectroscopic interest. The loss in this wavelength region ranges from 1-10 decibels/meter. These fibers are available from Infrared Fiber Systems Inc. of Silver Spring, Md., either without cladding or with cladding removed along specified lengths. Silver halide fibers with a wider spectral range and lower loss are available from Matsushita Corporation.

In implementing the invention, it should be noted that each fiber 20 (or fiber bundle) must be supported at a number of places (for simplification, not shown in FIG. 1). The supporting material 29 (FIGS. 2 and 3) should not introduce absorptions of sufficient magnitude to significantly reduce the IR power transmitted by the fibers. These objectives can be achieved by providing fibers with cladding only at the fiber support points, or by mounting the unclad fibers in a support material whose IR absorption range falls outside the wavelength regions used to measure contaminants. Because of their small dimension, fibers 20 can be mounted inside HDA 11 in such a way that airflow is unaffected - a great advantage when compared to particle filtering arrangements. Parts of the fiber loop can be placed at strategic locations in the HDA, such as on or behind an air bearing slider (not shown).

Figure 4:
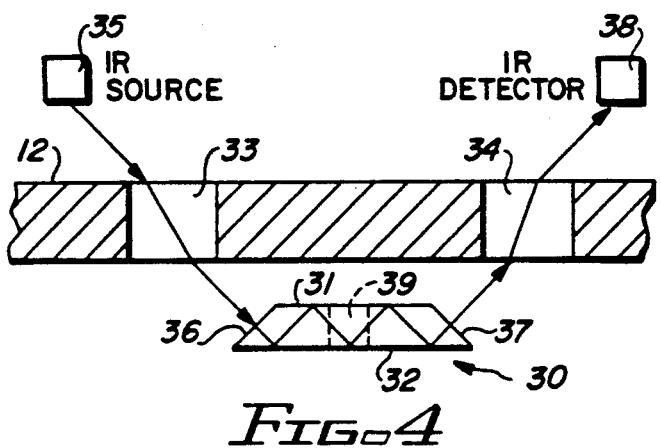
FIG. 4 is a fragmentary view, also to enlarged scale, of an alternative implementation of the invention utilizing an attenuated total reflection crystal.

As illustrated in FIG. 4, the invention can also be implemented by mounting a clean ATR crystal 30 within housing 12 such that both of its opposite sampling faces 31,32 are exposed to the airspace within the housing. ATR crystals are available from Spectra-Tech Inc. of Stamford, Conn. Windows 33,34 are provided in the wall of the housing. IR radiation is applied from an IR source 35 via window 33 onto a coupling face 36 and transmitted along the crystal. The transmitted radiation exits from a coupling face 37 of the crystal and is optically coupled via window 34 to an IR radiation detector 38. Detector 38 identifies and quantifies the airborne contaminants that settle on the sampling faces 31,32 from the changes in the spectrum of the IR radiation from its initial reference spectrum due to contamination. Thus, IR radiation optically coupled from outside the housing to ATR crystal 30 within the housing is optically coupled back from the crystal to a detector 38 outside the housing. Supporting material supports crystal 30 by contact with opposite faces (only one, 39, of which is shown) that are orthogonal to faces 36,37.

As a variation of the embodiment of FIG. 4, one coupling face (36) of crystal 30 is provided with a reflectance coating; the IR source 35 is eliminated; and the noncoated coupling face of the crystal is optically coupled to an IR spectrometer (like 24) to detect the IR emission originating from the sampling face(s) of the crystal.

It has thus far been assumed that the optical fibers 20 and ATR crystal 30 have been clean when installed; and that in their initial clean state, they each output to a spectrometer or detector a respective reference spectrum when optically coupled to a source of IR radiation. The reference spectra are stored and compared, as desired, with the spectra output as detected from time to time in response to IR radiation.

Periodically, each fiber 20 or crystal 30 can be cleaned by removing it and subjecting it to a high temperature, such as about 200° C., or cleaning it by some other means; whereupon the reference spectrum of the fiber or crystal would be again stored as a reference against which subsequent spectra of the output IR radiation can be compared to identify contaminants.

Other variations of the disclosed embodiments would include inserting a clean reference fiber or one side of the ATR crystal in a separate, sealed clean reference environment not affected by contamination to provide the reference spectrum against which the detected IR radiation is compared. Or, the fiber or crystal may be mounted in a cartridge or the like that is removable periodically from the housing for cleaning and resensing (or recalibration) of its reference spectrum.

Also, if desired, the fiber 20 or crystal 30 may be provided with a surface treatment or coating which traps contaminants by physical or chemical means such as sticking or absorption, or a chemical reaction forming a detectable compound. Moreover, the attenuated total reflection surface may be either under or over such a surface treatment or coating.

While the invention has been shown and described as implemented with a disk file having an HDA in a substantially sealed housing, it will be understood by those skilled in the art that the invention can be used wherever in situ chemical analysis of airborne contaminants is required in a substantially sealed environment without interrupting operation of any device within the sealed environment. Changes in form and detail may be made in the disclosed embodiments without departing from the scope and teaching of the invention. Accordingly, the apparatus and method herein disclosed are to be considered merely as illustrative, and the invention is to be limited only as specified in the claims.

We claim:

1. A disk file comprising:
   a head disk assembly;
   a housing providing a substantially sealed enclosure for the assembly; and
   an infrared (IR)-transparent attenuated total reflection element disposed within the enclosure and accessible from outside the enclosure for use in optically identifying airborne contaminants that settle on the element.

2. The disk file of claim 1 wherein the element is an optical fiber.

3. The disk file of claim 1 wherein the element is an optical fiber bundle.

4. The disk file of claim 1 wherein the element is an attenuated total reflection crystal.

5. The disk file of claim 1, further comprising a continuous source and an IR spectrometer, each accessible to said element.

6. The disk file of claim 1, further comprising a diode laser and an IR radiation detector, each accessible to said element.

7. The disk file of claim 1 wherein the contaminants are aerosols and/or vapors.

8. A disk file including a head-disk assembly contained within a substantially sealed housing, said disk file comprising:
   an infrared (IR)-transparent fiber disposed within the housing to collect airborne contaminants;
   a source of IR radiation outside the housing optically coupled to one end of the fiber; and
   means including an IR spectrometer optically coupled to the other end of the fiber for measuring, in situ and without interrupting operation of the disk file, contaminants that settle on the portion of the fiber contained within the housing.

9. A disk file including a head-disk assembly contained within a substantially sealed housing, said disk file comprising:
   an attenuated total reflection (ATR) crystal mounted with at least one sampling face exposed to the interior of the housing;
   means for applying IR radiation to a coupling face of said crystal; and
   means for sensing the IR radiation emitted from another coupling face of said crystal, thereby to measure, in situ, and without interrupting operation of the disk file, contaminants that settle on each sampling face of the crystal.

10. A disk file comprising:
    a head disk assembly;
    a housing providing a substantially sealed enclosure for the assembly to prevent exchange of air between the housing interior and the air exterior to the housing;
    an infrared (IR)-transparent attenuated total reflection element disposed within said enclosure to collect contaminants;
    an IR source optically coupled to the element; and
    an IR detector optically coupled to the element, said detector being responsive to changes in intensity of the IR radiation wavelengths transmitted by the element and absorbed by the contaminants to identify the contaminants and quantities thereof that settle on the element.

11. The disk file of claim 10, wherein the element has a surface treatment which traps contaminants.

12. The disk file of claim 11 wherein the element is an optical fiber.

13. The disk file of claim 11 wherein the element is an optical fiber bundle.

14. The disk file of claim 11 wherein the element is an attenuated total reflection crystal.

15. The disk file of claim 11 wherein the source is a continuous source and the detector is an IR spectrometer.

16. The disk file of claim 11 wherein the source is a diode laser and the detector is an IR radiation detector.

17. The disk file of claim 11 wherein the contaminants are aerosols and/or vapors.

18. The disk file of claim 10 wherein the element is an optical fiber.

19. The disk file of claim 10 wherein the element is an optical fiber bundle.

20. The disk file of claim 10 wherein the element is an attenuated total reflection crystal.

21. The disk file of claim 10 wherein the source is a continuous source and the detector is an IR spectrometer.

22. The disk file of claim 10 wherein the source is a diode laser and the detector is an IR radiation detector.

23. The disk file of claim 10 wherein the contaminants are aerosols and/or vapors.

24. A disk file comprising:
    a head disk assembly;
    a housing providing a substantially sealed enclosure for the assembly to prevent exchange of air between the housing interior and the air exterior to the housing;
    an infrared (IR)-transparent attenuated total reflection element having a surface treatment, said element disposed within said enclosure to react with contaminants to form a compound;
    an IR source optically coupled to the element; and
    an IR detector optically coupled to the element, said detector being responsive to changes in intensity of the IR radiation wavelengths transmitted by the element and absorbed by the compound formed on the element to identify the contaminants and quantities thereof.

25. The disk file of claim 24 wherein the element is an optical fiber.

26. The disk file of claim 24 wherein the element is an optical fiber bundle.

27. The disk file of claim 24 wherein the element is an attenuated total reflection crystal.

28. The disk file of claim 24 wherein the source is a continuous source and the detector is an IR spectrometer.

29. The disk file of claim 24 wherein the source is a diode laser and the detector is an IR radiation detector.

30. The disk file of claim 24 wherein the contaminants are aerosols and/or vapors.

31. Means for collecting and measuring airborne contaminants, in situ, within a disk file including a head-disk assembly contained within a substantially sealed housing, comprising:
    an infrared (IR)-transparent attenuated total reflection element disposed within the housing providing a surface on which contaminants collect, said element optically coupled to an IR source and further optically coupled to an IR detector, to enable identification and measurement of the contaminants that settle on the element by measuring changes in intensity of the wavelengths of IR radiation transmitted by the element.

32. Means for measuring airborne contaminants, in situ, within a disk file including a head-disk assembly contained within a substantially sealed housing, comprising:

an infrared (IR)-transparent attenuated total reflection element having a treated surface with which contaminants react to form compounds, disposed within the housing, said element optically coupled to an IR source and further optically coupled to an IR detector, to enable identification and measurement of the compounds that form on the element by measuring changes in intensity of the wavelengths of IR radiation transmitted by the element.

33. A method for detecting and measuring, in situ, airborne contaminants within a disk file including a head-disk assembly contained within a substantially sealed housing, comprising the steps of:

insertion of an infrared (IR)-transparent attenuated total reflection element into the housing to collect contaminants;

optically coupling the element to a source of IR radiation outside the housing; and coupling IR radiation exiting the element to an IR spectrometer to identify the contaminants and quantities thereof that settle on the element.

34. The method of claim 33, including the step of:

prior to the insertion step, providing the element with a surface treatment that enhances its ability to trap the contaminants.

35. The method of claim 34 further including the step of:

cleaning of the element periodically to restore it to an initial reference condition.

36. The method of claim 33 further including the step of:

cleaning of the element periodically to restore it to an initial reference condition.

37. A method for detecting and measuring, in situ, airborne contaminants within a disk file including a head-disk assembly contained within a substantially sealed housing, comprising the steps of:

providing an infrared (IR)-transparent attenuated total reflection element with a surface treatment which reacts chemically with contaminants;

insertion of the element into the housing;

optically coupling the element to a source of IR radiation outside the enclosure; and coupling IR radiation exiting the element to an IR spectrometer to identify compounds that form on the element as a result of the surface treatment reacting with the contaminants.

38. The method of claim 37 further including the step of:

cleaning the element periodically to restore it to an initial reference condition.

* * * * *